United States Patent
Wenning et al.

(10) Patent No.: US 8,480,985 B2
(45) Date of Patent: Jul. 9, 2013

(54) PROCESS AND DEVICE FOR DECOMPOSING LAUGHING GAS

(75) Inventors: Ulrike Wenning, Pullach (DE); Hans-Jörg Zander, München (DE); Anton Wellenhofer, Hohenschäftlarn (DE); Karl-Heinz Hofmann, Germering (DE); Wibke Korn, Munich (DE); Franz Beran, Munich (DE); Nicole Schödel, Munich (DE); Wolfgang Schmehl, Hamburg (DE)

(73) Assignee: Linde Aktiengesellschaft, München (DE)

( * ) Notice: Subject to any disclaimer, the term of this patent is extended or adjusted under 35 U.S.C. 154(b) by 0 days.

(21) Appl. No.: 13/144,227

(22) PCT Filed: Jan. 5, 2010

(86) PCT No.: PCT/EP2010/000014
§ 371 (c)(1),
(2), (4) Date: Oct. 6, 2011

(87) PCT Pub. No.: WO2010/081643
PCT Pub. Date: Jul. 22, 2010

(65) Prior Publication Data
US 2012/0063982 A1    Mar. 15, 2012

(30) Foreign Application Priority Data

Jan. 13, 2009  (DE) .................. 10 2009 004 431
Aug. 13, 2009  (DE) .................. 10 2009 037 885

(51) Int. Cl.
*B01D 53/56*    (2006.01)
*B01D 53/74*    (2006.01)
*B01D 53/86*    (2006.01)

(52) U.S. Cl.
USPC ......... 423/239.1; 422/168; 422/177; 422/180

(58) Field of Classification Search
USPC .............. 423/239.1; 422/168, 177, 180
See application file for complete search history.

(56) References Cited

U.S. PATENT DOCUMENTS 6,056,928 A * 5/2000 Fetzer et al. ............... 423/235
2005/0281724 A1 * 12/2005 Hotta et al. ................ 423/239.1
(Continued)

FOREIGN PATENT DOCUMENTS

| EP | 2165756 | 3/2010 |
| JP | 55 031463 | 3/1980 |
| WO | WO 02/26355 | 4/2002 |
| WO | WO 2006/059506 | 6/2006 |

OTHER PUBLICATIONS

International Search Report mailed Apr. 19, 2010 for corresponding International Patent Application No. PCT/EP2010/000014.

(Continued)

*Primary Examiner* — Timothy Vanoy
(74) *Attorney, Agent, or Firm* — Swanson & Bratschun, L.L.C.

(57) ABSTRACT

A method and device for the catalytic decomposition of laughing gas in a laughing-gas-bearing gas. The method includes diluting the laughing-gas-bearing gas with a diluting gas, while forming a laughing-gas-bearing charge gas. The laughing-gas bearing charge gas is passed through a heat-exchange step where heat exchange occurs with an exhaust. A heating step occurs for occasional heating of the laughing-gas-bearing charge gas in a fixed-bed reactor for catalytic decomposition of the laughing gas. In some embodiments the diluting gas is dried, and at least a part of the exhaust from the catalytic decomposition of the laughing gas is mixed with the laughing-gas-bearing charge gas upstream of the catalytic decomposition of the laughing gas.

9 Claims, 1 Drawing Sheet

U.S. PATENT DOCUMENTS

2008/0241034 A1* 10/2008 Schwefer et al. .......... 423/239.2
2010/0196238 A1* 8/2010 Fujiwara .................... 423/239.1
2010/0209325 A1* 8/2010 Schwefer et al. .......... 423/239.1
2010/0303699 A1* 12/2010 Sasaki ....................... 423/239.2
2012/0014855 A1* 1/2012 Beran et al. ............... 423/239.1

OTHER PUBLICATIONS

English translation of the International Preliminary Report on Patentability mailed Jul. 14, 2011 for corresponding International Patent Application No. PCT/EP2010/000014.

* cited by examiner

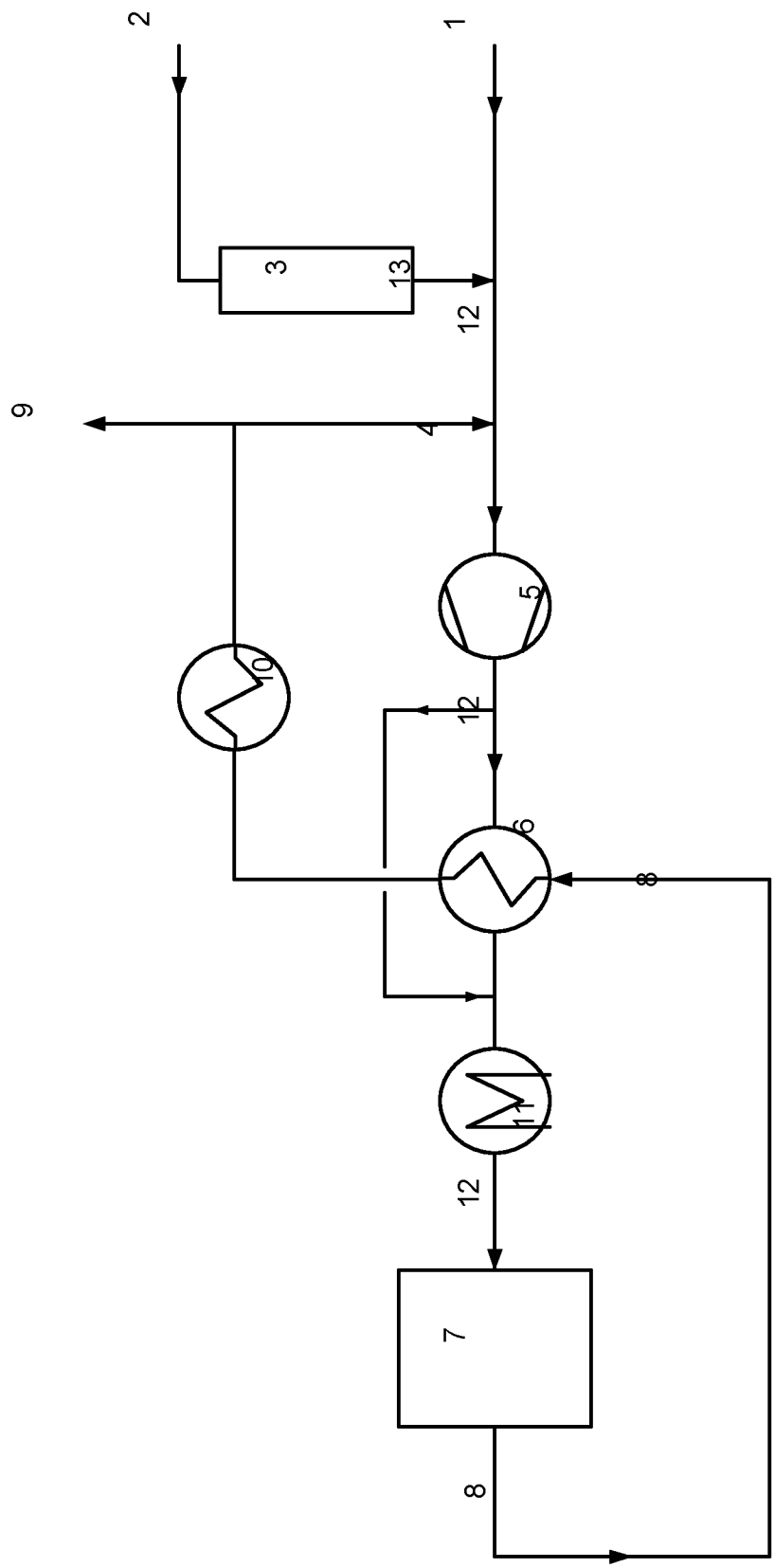

PROCESS AND DEVICE FOR DECOMPOSING LAUGHING GAS

RELATED APPLICATIONS

This application is a 35 U.S.C. §371 national phase application of PCT/EP2010/000014 (WO 2010/081643), filed on Jan. 5, 2010, entitled "PROCESS AND DEVICE FOR DECOMPOSING LAUGHING GAS", which application claims the benefit of German Application Serial No. 10 2009 004 431.0, filed Jan. 13, 2009, and German Application Serial No. 10 2009 037 885.5, filed Aug. 13, 2009, which is incorporated herein by reference in its entirety.

The invention concerns a method for catalytic decomposition of laughing gas in a laughing-gas-bearing gas, wherein the laughing-gas-bearing gas is diluted with a diluting gas in forming a laughing-gas-bearing charge gas and is passed through a heat-exchange step in heat exchange with an exhaust and a heating step for the occasional heating of the laughing-gas-bearing charge gas into a fixed-bed reactor for catalytic decomposition of laughing gas, as well as a device for carrying out the method. Such a method and such a device are known, for example, from the U.S. Pat. No. 7,235,222, US patent application 2006/0008401, or WO 2006/059506.

Nitrous oxide or laughing gas is a non-poisonous gas, which has long been used as an anesthetic or analgesic agent alone or in combination with other substances. In addition, laughing gas also originates as a by-product in the manufacture of nitric acid or is used in organic syntheses. A problem exists in application as an anesthetic or analgesic agent, in that the laughing gas exhaled by the patient can be concentrated in the treatment space above the current maximally permissible workplace concentration. Such concentrated laughing gas can lead over a long time to an excessive burden for medical personnel.

Additionally, laughing gas also contributes in a considerable amount to the greenhouse effect and to breakdown of the ozone layer. Hence from the point of view of environmental technology, decomposition of laughing gas is necessary before release into the atmosphere.

There is in prior art a demand for a method of effective decomposition of laughing gas from various sources, be it from medical treatments, nitric-acid production, exhausts from various organic syntheses, in the cleaning/evacuation of gas cylinders, or from exhaust streams in the very manufacture of laughing gas.

The patents and patent applications cited above deal with the recovery of laughing gas from medical applications and essentially propose collecting the laughing gas that accumulates in several treatment or operating spaces of a hospital complex and purifying in a common catalytic treatment. Catalysts are preferably used for this which make decomposition of the laughing gas possible at relatively low temperatures, that is, below 600° C. Different adsorbents in the catalytic treatment can be connected in series in order to separate out disruptive components such as sevofluorane, desfluorane, isofluorane, halothane, or other halogenated hydrocarbons.

In addition, a method and a device for decomposition of laughing gas has been proposed by the inventors of the present application in the unpublished European patent application EP 08164753.9, which provides for transferring laughing gas accumulated directly on site in the treatment room for an individual patient, and thus avoids expensive collection of the different streams of laughing gas within the hospital complex.

Commercially available methods for laughing-gas removal in prior art are based mainly on thermal or catalytic decomposition of laughing gas at more than 800° C.

More modern catalytic methods, which operate at temperatures below 600° C., are a common problem, namely that the decomposition of laughing gas is highly exothermic. This means that if the gas exhaled by the patient is subject to no further pre-processing for catalytic decomposition, then, due to the high laughing-gas concentration of up to 70%, such a high exothermic reaction or heat development at the catalyst indicates that this is irreversibly damaging. Hence the current methods for removing laughing gas, as have been previously stated, have the common feature that the gas stream is diluted with another laughing-gas-free gas to a laughing-gas concentration of usually less than 5%. In addition, measures are accordingly provided for the catalyst to be able to operate isothermally, that is, to be cooled or heated.

The task of the present invention is based on a method for improving of the sort mentioned at the beginning, so that a flexible decomposition of laughing gas in a laughing-gas-bearing gas is possible, without intensely increasing the temperature of the laughing-gas decomposition and thus positively affecting the catalyst service life.

The present task is resolved with respect to method by the combination of characteristics cited in the features of claim 1. Further advantageous embodiments of the invention are cited in the subclaims.

According to the invention, the diluting gas, which is added to the laughing-gas-bearing gas, is dry. Additionally, at least a part of the exhaust from the catalytic decomposition of laughing gas is mixed into with the diluted laughing-gas-bearing charge gas upstream of the catalytic laughing-gas decomposition.

The invention considers any laughing-gas-bearing gas stream to be within the scope of a laughing-gas-bearing gas. This can be, for one thing, a laughing gas exhaled by a patient within the scope of a medical application, or for another thing, an exhaust stream from production or filling cylinders of laughing gas, for instance. The invention is suited to treating any gas streams that contain laughing gas in any concentration.

Through the method according to the invention, it is ensured that the laughing-gas-bearing charge gas contains no or only a small portion of water before supplying it for catalytic decomposition of the laughing gas. The start-up temperature of catalytic laughing-gas decomposition with a dry gas clearly lies below the start-up temperature for a gas that contains water. This has the advantage, for one thing, that the charge gas in the catalytic decomposition reaction does not have to be heated up as much. For another thing, the temperature difference between the start-up temperature and the maximum permissible temperature for the catalyst or accessory compartments can be higher. Hence laughing-gas-bearing charge gases in the catalytic decomposition can also be processed with a higher share of laughing gas.

Through the dilution according to the invention of the laughing-gas-bearing gas with dry diluting gas and the further mixing of at least a part of the exhaust gas from the catalytic laughing-gas decomposition, it is ensured that the exhaust gas from catalytic laughing-gas decomposition is always nearly dry. By feeding back the nearly dry exhaust from the catalytic decomposition of the laughing gas and mixing it into the laughing-gas-bearing charge gas, the portion of dry diluting gas needed is minimized. Thus very stable processing is made possible. A part of the exhaust fed back is given off to the atmosphere before mixing with the laughing-gas-bearing charge gas.

By diluting the laughing-gas-bearing charge gas according to the invention with the dried diluting gas and mixing at least a part of the exhaust from the catalytic decomposition of the laughing gas, a more favorable and lower reaction temperature is used in the method according to the invention with the same laughing-gas conversion as in prior art. As a result, the materials selected are adapted to the lower reaction temperature. Additionally, the method according to the invention allows operation at the same conversion with a smaller reactor volume. This is a particular advantage, together with the expanded spectrum of possible materials, for application to laughing-gas decomposition in a clinic. Through the method according to the invention, the decomposition of laughing gas can be directly carried out on small and compact equipment in a treatment space.

In accordance with the method according to the invention, the moisture content in the total gas stream, which is passed as a charge stream in the catalytic decomposition of the laughing gas, is held constant by the diluting gas. By diluting the laughing-gas-bearing gas with the dry diluting gas and by mixing at least a part of the exhaust, the laughing-gas-bearing gas can itself also contain moisture up to saturation. The charge stream for the catalytic decomposition of laughing gas is always nearly dry. This leads to a stable reaction and therefore to minimal measurement, control, and regulation expense. As a result, the degree of the overall effect and therewith the economy of the method are increased.

The advantages cited for the method according to the invention occur in both isothermal and adiabatic reactions of catalytic laughing-gas decomposition.

The flexibility of the catalytic decomposition of laughing gas clearly increases through the method according to the invention. For one thing, the breadth of variation related to a temperature increase is clearly greater due to a greater share of laughing gas in the laughing-gas-bearing charge gas as a result of reduced reaction temperature with the method according to the invention. For another thing, the concentration of the laughing gas in the laughing-gas-bearing charge gas can be readily regulated before catalytic decomposition of the laughing gas by supplying dry diluting gas. Through the combination according to the invention of supplying dry diluting gas and mixing at least a part of the exhaust from the catalytic decomposition of the laughing gas, only a small amount of dry diluting gas is needed in the method's normal operation. This amount can simply be increased for an increased concentration of laughing gas in the laughing-gas-bearing charge gas.

Advantageously, noble-metal catalysts are used as a catalyst on carrier materials for the conversion according to the method according to the invention. Palladium, rhodium, platinum, and ruthenium, for example, number among the advantageous noble metals here, wherein palladium and rhodium are especially preferred. Materials known in prior art known, such as aluminum oxide, silicon oxide, or zeolite, for example, are appropriately used as carrier materials.

Air or an inert gas is preferred as a diluting gas. Air is cost-effective and available without limit. Just like the preferred inert gases, air does not affect the reaction of catalytic laughing-gas decomposition. Hence, air or an inert gas is outstandingly suited as a diluting gas.

Preferably, the diluting gas is dried so that the laughing-gas-bearing charge gas exhibits a dew point of −20° C., and especially preferably −40° C. A moisture content in the laughing-gas-bearing charge gas that corresponds to a dew point of −20° C., preferably −40° C., is sufficient to use the method according to the invention to full advantage.

In one embodiment of the invention, the mixing of the exhaust takes place in laughing-gas-bearing charge gas upstream of the heat-exchange step and of heat exchange with the exhaust. In this embodiment of the invention, the exhaust from the catalytic decomposition of the laughing gas passes through the heat exchanger before it is mixed with the laughing-gas-bearing charge gas. The diluted laughing-gas-bearing charge stream is then passed with the mixed exhaust through the same heat exchanger into the reactor for catalytic decomposition of the laughing gas. Thus, in this embodiment of the invention, a heat exchanger is used for cooling the exhaust and at the same time heating the laughing-gas-bearing charge gas.

Alternatively, the hot exhaust can be passed at least partially directly into the laughing-gas-bearing charge gas.

In another embodiment of the invention, the laughing-gas-bearing charge gas is dried after supplying the diluting air to the laughing-gas-bearing charge gas.

The drying of the diluting gas appropriately takes place with a single-pass dryer, a molecular sieve, an adsorbent, an exchange-bed adsorbent, or a diaphragm dryer. The means cited for drying the diluting gas are established in prior art and present different advantages. Single-pass dryers are an established and favorable means of drying a charge gas. Through the method according to the invention, only a small amount has to be dried in the diluting gas. Hence it is also sufficient to replace the single-pass dryer at longer intervals. Adsorbents or molecular sieves have to be regenerated. With a small amount of the diluting gas to be dried, this regeneration is only required at longer intervals. Exchange-bed adsorbents can be use to ensure continuous operation of the method. In that case, an adsorbent is used for drying the diluting gas, while at the same time a further adsorbent is regenerated. In an advantageous embodiment, hot exhaust from the catalytic decomposition of the laughing gas is used to regenerate the adsorbent(s).

In another embodiment of the invention, the laughing-gas-bearing gas can still be additionally supplied to a separate step before dilution for drying or for cleaning out of halogen-bearing compounds.

Advantageously, the laughing-gas concentration in the laughing-gas-bearing charge gas is measured before and/or after the dilution with the diluting gas and/or right in front of the reactor. On the basis of this measurement, the reaction temperature, the temperature of the laughing-gas-bearing charge gas, the mixed amount of diluting gas, and/or the mixed amount of exhaust are regulated. There can also advantageously be a bypass valve for controlling the temperature of the laughing-gas-bearing charge gas, in order to use the heat exchanger for heat exchange between the laughing-gas-bearing charge gas and the hot exhaust.

In one embodiment of the invention, several laughing-gas-bearing charge streams are collected in a gas receptacle and from there passed as a charge stream in the method according to the invention. This embodiment of the invention is especially suited for production systems, tanks of laughing gas, or cylinder filling. In such application cases, there is for the most part exhaust piping for the laughing-gas-bearing gas streams. In this embodiment of the invention, the existing piping is connected to a low-pressure gas receptacle. All the laughing-gas-bearing gas streams are collected in the low-pressure gas receptacle. Then the laughing-gas-bearing gas is removed from the gas receptacle and is passed as a charge stream in the method according to the invention. In this way, fluctuations in the amount of an individual gas stream can be brought under control by the gas receptacle.

As for the device, the task set is resolved through the characteristic features of claim 6.

The device according to the invention for catalytic decomposition of laughing gas includes a supply of laughing gas to a compressor, a heat exchanger, a heater, and a fixed-bed reactor which exhibits a catalyst and is suitable for catalytic decomposition of laughing gas, as well as piping in the supply to the compressor. According to the invention, the device further exhibits an engineered flow connection between the exhaust outlet of the fixed-bed reactor and the supply to the compressor, which leads through the heat exchanger. According to the invention, the piping is connected to a dryer, which is suitable for drying a diluting gas.

With the present invention, it succeeds in particularly ensuring a stable procedure. It can thereby react flexibly at different concentrations of laughing gas in laughing-gas-bearing charge gas. The start-up temperature and the reaction temperature of the catalytic decomposition of laughing gas can, in contrast to a method according to prior art, clearly be chosen to be lower.

The invention will be clarified in more detail in the following using an embodiment example represented in the FIGURE.

It shows

FIG. 1 an embodiment example of the method according to the invention and the device according to the invention.

FIG. 1 shows an embodiment example of the method according to the invention and the device according to the invention for catalytic decomposition 7 of laughing gas in a laughing-gas-bearing gas 1. The laughing-gas-bearing gas 1 is diluted by means of a diluting gas 2. According to the invention, the diluting gas 2 is nearly rid of its share of water in the dryer 3. In this embodiment of the invention, air is used as a diluting gas 2. After supplying the diluting gas 2 through the piping 13, the exhaust 8 from the catalytic decomposition 7 is mixed 4 with the laughing-gas-bearing charge gas 12. After mixing 4 the exhaust 8 from the catalytic decomposition 7 of the laughing gas, the laughing-gas-bearing charge gas 12 is compressed 5, and passed into the heat exchanger 6. In the heat exchanger 6, the laughing-gas-bearing charge gas 12 is heated by heat exchange with the exhaust 8. The exhaust 8 is cooled off at the same time in the heat exchanger 6. The heated, laughing-gas-bearing charge gas 12 is passed through a further, optional heater 11 as a charge in the catalytic decomposition 7 of the laughing gas. The heater 11 is used only for additional, optional heating of the laughing-gas-bearing charge gas 12. The inlet temperature in the catalytic decomposition of laughing gas in this embodiment of the invention is roughly at 350° C. The catalytic decomposition of the laughing gas hereby occurs at atmospheric pressure or a little higher pressure. A part of the exhaust 8 is taken out of the process. The exhaust 8 is further cooled by a further, optional heat exchanger 10. Through the additional cooling by means of the heat exchanger 10, it is ensured that the next pieces of equipment, such as the compressor, are protected from overheating. The embodiment example represented is suited for use in a treatment space and for the decomposition of laughing gas from a medical treatment. Through the heat exchanger 10, the permissible temperature for the part of the exhaust 8 that is given off 9 to the atmosphere can also be monitored here. For optimal control of the inlet temperature of the laughing-gas-bearing charge gas 12 in the catalytic decomposition 7 of laughing gas, at least a part of the laughing-gas-bearing charge gas 12 can be passed on to the heat exchanger 6 with a bypass valve 14.

The invention claimed is:

1. A method for catalytic decomposition of laughing gas in a laughing-gas-bearing gas, wherein the laughing-gas-bearing gas is diluted with a diluting gas, while forming a laughing-gas-bearing charge gas and is passed through a heat-exchange step during heat exchange with an exhaust and a heating step for occasional heating of the laughing-gas-bearing charge gas in a fixed-bed reactor for catalytic decomposition of the laughing gas, characterized in that the diluting gas, which is added to the laughing-gas-bearing gas and is dried, and at least a part of the exhaust from the catalytic decomposition of the laughing gas is mixed with the laughing-gas-bearing charge gas upstream of the catalytic decomposition of the laughing gas.

2. A method according to claim 1, characterized in that air or an inert gas is used as a diluting gas.

3. A method according to claim 1, characterized in that the diluting gas is dried so that the laughing-gas-bearing charge gas exhibits a dew point of −20° C.

4. A method according to claim 1, characterized in that the mixing of the exhaust into the laughing-gas-bearing charge gas takes place upstream of the heat-exchange step and of heat exchange with the exhaust.

5. A method according to claim 1, characterized in that drying of the diluting gas takes place with a single-pass dryer, a molecular sieve, an adsorbent, an exchange-bed adsorbent, or a diaphragm dryer.

6. A method according to claim 1, characterized in that at least a part of the exhaust is passed directly into the laughing-gas-bearing charge gas.

7. A method according to claim 1, characterized in that several laughing-gas-bearing gas streams are collected in a gas receptacle and are removed to it as a laughing-gas-bearing gas.

8. A device for catalytic decomposition of laughing gas comprising a supply of the laughing-gas-bearing charge gas to a compressor, a heat exchanger, a heater, and a fixed-bed reactor which exhibits a catalyst and is suitable for catalytic decomposition of laughing gas, as well as piping in the supply for the compressor, characterized in that the device exhibits an engineered flow connection between the exhaust outlet of the fixed-bed reactor and the supply to the compressor, which leads to the heat exchanger, and the piping is connected to a dryer suitable for drying a diluting gas.

9. A method according to claim 1, characterized in that the diluting gas is dried so that the laughing-gas-bearing charge gas exhibits a dew point of −40° C.

* * * * *